United States Patent [19]

Spielvogel et al.

[11] Patent Number: 4,647,555

[45] Date of Patent: Mar. 3, 1987

[54] ESTERS OF BORON ANALOGUES OF AMINO ACIDS

[75] Inventors: Bernard F. Spielvogel, Wake County; Andrew T. McPhail, Durham; Iris H. Hall, Chapel Hill, all of N.C.

[73] Assignee: The United States of America as represented by the Secretary of the Army, Washington, D.C.

[21] Appl. No.: 664,647

[22] Filed: Oct. 25, 1984

[51] Int. Cl.$^4$ .................. A61K 31/695; A61L 23/00; A01N 55/00; C07F 5/02
[52] U.S. Cl. ..................................... 514/63; 556/402; 560/20; 560/130; 560/156; 260/397.2
[58] Field of Search .................. 556/402; 560/20, 130, 560/156; 260/397.2; 424/184; 514/63

[56] References Cited

U.S. PATENT DOCUMENTS

| | | | |
|---|---|---|---|
| 3,018,299 | 1/1962 | Pike | 556/402 |
| 3,265,737 | 8/1966 | Miller | 556/402 X |
| 4,035,409 | 7/1977 | Cummings | 560/130 X |
| 4,440,941 | 4/1984 | Suh et al. | 560/20 |

*Primary Examiner*—Paul F. Shaver
*Attorney, Agent, or Firm*—Peter A. Taucher; Gail S. Soderling

[57] ABSTRACT

Ester analogues of boron analogues of amino acid are disclosed. Also disclosed is a method of forming the ester analogues in high yield by condensation of the corresponding acids and alcohols with dicylohexylcarbodiimide at room temperature in dichloromethane. The disclosed compounds have shown interesting biological activities, in particular, hypolipidemic activity as well as significant antitumor and antiarthritic activities.

14 Claims, No Drawings

ESTERS OF BORON ANALOGUES OF AMINO ACIDS

GOVERNMENT INTEREST

The invention described herein may be manufactured, used, and licensed by or for the Government for governmental purposes without payment to me of any royalty.

BACKGROUND OF THE INVENTION

In one aspect this invention relates to boron analogues of amino acids. In a further aspect, this invention relates to methods of forming esters of boron analogues of amino acids. In yet a further aspect, this invention relates to the use of boron analogues of amino acids as a biologically active material for antitumor or hypolipidemic activity.

Boron analogues of amino acids are broadly known in the art. The antihyperlipidemic activity of amino cyanoboranes is discussed in Antihyperlipidemic Activity of Amino Cyanoboranes, Amino Carboxyboranes and Related Compounds, *Journal of Pharmaceutical Sciences*, V. 70 no. 3 March 1981.

Issued U.S. Patents related to boron analogues of amino acids include U.S. Pat. Nos. 4,209,510; 4,312,989; and 4,368,194.

SUMMARY OF THE INVENTION

This invention is directed to a series of esters derived from boron analogues of amino acids and having the general formulation $R_1R_2R_3NBH_2COOR_4$ wherein $R_1$, $R_2$ and $R_3$ are selected from the class comprising hydrogen and lower alkyls having from one to eight carbon atoms and $R_4$ is lower alkyl or haloalkyl having one to eight carbon atoms. The alkyl groups can be straight or branched chains. Representative alkyl groups include methyl, ethyl, propyl and n-butyl. In general, the preferred moieties are methyl and ethyl groups because these moieties have minimal steric hindrance during synthesis.

Compounds of this invention can be prepared condensing the corresponding acids and alcohols with dicyclohexylcarbodiimide (DCC) at room temperature in dichloromethane and using a method disclosed hereinafter.

DESCRIPTION OF PREFERRED EMBODIMENTS

Preparation of Representative Ester Materials:

1. Trimethylamine-carbethoxyborane $(CH_3)_3N.BH_2COOC_2H_5$, was prepared by dehydrating a solution of $(CH_3)_3N.BH_2COOH$ and absolute ethanol with DCC at room temperature for 6 days. This procedure resulted in a 45% yield. The relatively high volatility and solubility in water of this sweet-smelling ester probably contributed to its low yield in this procedure.

2. Trimethylamine-carbomethoxyborane, $(CH_3)_3N.BH_2COOCH_3$, was prepared with an 82% yield by condensing $(CH_3)_3N.BH_2COOH$ and $CH_3OH$ with DCC at room temperature for one week; extension of the reaction period to two weeks led to an increase in the yield to 98%.

3. Dimethylamine-carbomethoxyborane, $(CH_3)_2NH.BH_2COOCH_3$, was prepared in 67% yield by an amine-exchange reaction of $(CH_3)_3N.BH_2COOCH_3$ with an 8-fold excess (by weight) of $(CH_3)_2NH$ in a glass pressure reaction vessel for 2 weeks at room temperature. The 8% unreacted starting ester in the product mixture was removed by washing with $H_2O$ and vacuum pumping. The ester linkages in the starting material and product were not cleaved by the excess amine. As an alternative, condensing $(CH_3)_2NH.BH_2COOH$ and $CH_3OH$ with DCC at room temperature for 4 days could be performed. This reaction procedure gave a very low yield of (8%).

4. Methylamine-carbomethoxyborane, $CH_3NH_2.BH_2COOCH_3$ was prepared by condensing $CH_3NH_2.BH_2COOH$ and $CH_3OH$ with DCC at room temperature for 6 days. This reaction had a 21% yield.

5. Trimethylamine-(carbo-2-chloroethoxy)borane, $(CH_3)_3N.BH_2COOCH_2CH_2Cl$, was prepared in a manner similar to the preparation of compound 4 by condensing $(CH_3)_3N.BH_2COOH$ and $HOCH_2CH_2Cl$ with DCC at room temperature for 1 week. This reaction yielded 61%.

6. Ammonia-carboxmethoxyborane, $H_3N.BH_2COOCH_3$, was prepared by an amine-exchange reaction carried out in a stainless steel pressure vessel between $(CH_3)_3N.BH_2COOCH_3$ and excess liquid $NH_3$ at room temperature for 2 weeks.

7. Trimethylamine-(carbotrimethylsiloxy)borane, $(CH_3)_3N.BH_2COOSi(CH_3)_3$, was prepared by a procedure involving lithiation of $(CH_3)_3N.BH_2COOH$ with $n-C_4H_9Li$ under dry $N_2$ in ether and subsequent reaction of the lithium salt (not isolated) with $(CH_3)hd 3SiCl$ at ambient temperature for 16 hours. Work-up and vacuum distillation afforded 58% of the silyl ester as a clear, moisture-sensitive liquid that solidified on standing.

All of the new compounds were characterized by elemental analysis and IR, H NMR and B NMR spectroscopy. Physical and spectral data of the esters are given in Table I. IR spectra exhibited characteristic B—H and C=O absorptions; H and B NMR spectral data were consistent with the structures shown for the compounds. IR spectra were recorded on a Perkin-Elmer 297 spectrometer. Solid samples were prepared as KBr disks, as Nujol mulls between NaCl disks, or as solutions in suitable solvents; oils were recorded neat. Proton and boron NMR spectra were obtained on Varian EM 360A and JEOL FX 90Q spectrometers, respectively. Elemental analyses were performed by Galbraith Laboratories, Inc., Knoxville, TN, or Schwarzkopf Microanalytical Laboratory, Inc., Woodside, NY.

TABLE 1

| compd | ester | bp/mp, °C. | yield, % | shifts, ppm[a] | $J_{B-H}$, Hz |
|---|---|---|---|---|---|
| 1 | $(CH_3)_3N.BH_2COOC_2H_5$ | 45–47 | 34–41 | −9.17 (t) | 98 |
| 2 | $(CH_3)_3N.BH_2COOCH_3$ | 90–92 | 82–98 | −9.09 (t) | 99 |
| 3 | $(CH_3)_2NH.BH_2COOCH_3$ | 52–53 | 67 | −12.57 (t) | 95 |
| 4 | $CH_3NH_2BH_2COOCH_3$ | 56–57 | 21 | −16.22 (t) | 98 |
| 5 | $(CH_3)_3N.BH_2COOCH_2CH_2Cl$ | | 61 | −8.75 | 97 |
| 6 | $H_3N.BH_2COOCH_3$ | 92–93 | 49 | −20.45 (t) | 94 |

TABLE 1-continued

| compd | ester | bp/mp, °C. | yield, % | shifts, ppm[a] | $J_{B-H}$, Hz |
|---|---|---|---|---|---|
| 7 | $(CH_3)_3N.BH_2COOSi(CH_3)_3$ | 60(0.2 torr) | 58 | | |

[a] $(C_2H_5)_2O\cdot BF_3$ was used as an external standard; all chemical shifts reported here were (negative) upfield from the standard.

SERUM LIPID SCREENING $CF_1$ male mice (30 g) were fed rodent laboratory food with water ad libitum during the experiment. The compounds of this invention were suspended in 1% carboxymethylcellulose-water and homogenized. The doses were calculated on the weekly weights of the mice. Test compounds were administered at a rate of 8 mg/kg/day ip. On the 9th and 16th days, blood was collected by tail vein bleeding in alkali-free, nonheparinized microcapillary tubes and centrifuged 3 min to obtain the serum. Duplicate 30-ml samples of nonhemolyzed serum were used to determine the serum cholesterol levels (milligram percent) by a modification of the Liebermann-Burchard reaction described in Ness et al, Clin, Chem, Acta V. 10, p. 229 (1964). A separate group of mice were bled on day 14, and their serum triglyceride levels (milligram percent) were determined by using 25-ml samples.

The results of the serum testing are set forth in Table 2. The values given are percent control. The percentage inhibition, the effectiveness of the compound, is determined by subtracting the control percentage from 100.

TABLE 2

| | | Percentage Control of Cholesterol & Triglyceride | | |
|---|---|---|---|---|
| | | Serum Cholesterol | | Serum Triglyceride |
| Compound | I.P. Dose | Day 9 | Day 16 | Day 16 |
| $MeNH_2BH_2COOMe$ | 8 | 69 | — | — |
| $Me_3NBH_2COOMe$ | 8 | 79 | 58 | 23 |
| $Me_2NHBN_2COOMe$ | 8 | 73 | 68 | 69 |

All of the compounds show a degree of control on both serum cholesterol and triglycerides. In particular, trimethylaminecarbomethoxyborane showed an inhibition effect of 77% on serum triglycerides.

Alternative Ester Production Method

The formation of esters of the boron analogs of amino acids as set forth herein before has provided a technique for making sufficient quantities of material for testing. However, the reaction times for the production of the compounds by condensation of the corresponding acids and alcohols with DCC at room temperature in $CH_2Cl_2$. The reaction generally gives good to moderate yields but is time consuming, i.e., up to a week or more. Moreover, the esters contain dicyclohexylurea as a by-product which must be removed. Separation of the desired product by fractional chrystalization and solvent extraction is tedious and difficult owing to the similar solubility characteristics of the desired ester and the by products.

An alternative synthesis technique for making the ester is the treatment of trialkylaminecarboxyborane with a tetrafluroborate compound, as disclosed in U.S. Pat. No. 4,368,194, was effective for compounds where the initial carboxyborane had a triamine substituent. It does not work with carboxyboranes of diamines, monamine or ammonia since the hydrogens on the boron in the borane hydrolyze.

A more efficient synthesis with a more general application is disclosed. In general, the desired esters are formed by the reaction of mixed carboxylic-carbonic anhydrides under mild conditions. In the improved synthesis, mixing equimolar amounts amine-carboxyborane, alkylchloroformate, and trialklyl amine in methylene chloride at reduced temperatures, i. e., $-10°$ to $+10°$ C. produces a rapid decarboxylation to give ester product.

As an example, 0.01 mole of alkylchloroformate and 0.001 mole of dimethylaminopyridine were added to a solution of 0.01 mole of amine-carboxyborane and 0.011 mole of triethylamine in 100 ml of methylene chloride. The mixture was maintained at $0°$ C. for one hour with constant stirring. The reaction proceeded smoothly with the evolution of carbon dioxide. After one hour, the solution was given two washings with 20 ml of water and dried using magnesium sulfate. The resulting material was concentrated to pure ester.

Using various starting materials, esters of the basic configuration $(R)_3N.BH_2COOR'$ were made using various starting compounds. Esters were formed where R was methyl, ethyl, benzene (phenyl), and toluene (tolyl). The number of organic moieties attached to the amino nitrogen was varied from 1 to 3.

Esters were formed where R' was methyl, ethyl, cholesteryl, toluene (tolyl), benzene (phenyl), alkylsilyl, ethylbromide and ethylchloride.

This method allows a rapid production at high yields of a wide variety of ester materials.

From the foregoing description, it is apparent that a new class of esters formed from boron analogs of amino acids has been described. Further, a new and improved method of producing the esters has been disclosed. The esters show a utility in reducing serum cholesterol and triglycerides.

I wish it to be understood that I do not desire to be limited to the exact details of construction shown and described for obvious modifications will occur to a person skilled in the art, without departing from the spirit and scope of the appended claims.

What is claimed is:

1. An amine borane ester compound having the structure $R_1R_2R_3NBH_2COOR_4$, wherein $R_1$, $R_2$, and $R_3$ are chosen from the class consisting of lower alkyl having 1 to 8 carbon atoms, phenyl, tolyl, and hydrogen; and $R_4$ is chosen from the class consisting of lower alkyl having 1 to 8 carbon atoms, phenyl, tolyl, cholesteryl, alkylsilyl and lower haloalkyl having from 1 to 8 carbon atoms.

2. The compounds of claim 1 wherein $R_1R_2R_3$ are chosen from the class consisting of methyl and ethyl.

3. The compounds of claim 1 wherein $R_4$ is lower chosen from the class consisting of methyl and ethyl.

4. The compounds of claim 1 where $R_4$ is haloalkyl.

5. The compounds of claim 1 where $R_4$ is cholesteryl.

6. The compounds of claim 1 where $R_4$ is phenyl.

7. The compounds of claim 1 where $R_4$ is tolyl.

8. A method of forming an amine borane ester compound of the structure $R_1R_2R_3NBH_2COOR_4$, wherein $R_1R_2$ and $R_3$ are chosen from the class consisting of lower alkyl having 1 to 8 carbon attoms, phenyl, tolyl and hydrogen; $R_4$ is chosen from the class consisting of lower alkyl having 1 to 8 carbon atoms, phenyl, tolyl, alkylsilyl and lower haloalkyl having from 1 to 8 carbon atoms, comprising the steps of mixing equimolar amounts of amine-carboxyborane, alkylchloroformate and trialkyl amine in a compatible solvent; cooling the temperature of the reaction mixture; and agitating the reaction mixture until the reaction reaches equilibrium.

9. The method of claim 8 where the reaction mixture is maintained at room temperature.

10. The method of claim 8 where a catalytic amount of dimethyaminopyridine is added to the reaction mixture.

11. The method of claim 8 where the reaction temperature is maintained at $-10°$ to $+10°$ C.

12. A pharmaceutical composition for the inhibition of serum cholesterol or triglycerides in animals comprising as the active component a therapeutically effective amount of a compound according to claim 1 suspended and homogneized in a 1% solution of carboxymethylcellulose - water carrier.

13. An amine borane ester compound having the structure $R_1R_2R_3NBH_2COOR_4$ wherein $R_1$, $R_2$, and $R_3$ are chosen from the class consisting of lower alkyl having from 1 to 8 carbon atoms, phenyl, tolyl, and hydrogen and $R_4$ is an alkylsilyl.

14. A pharmaceutical composition for the inhibition of serum cholesterol or triglycerides in animals comprising as the active component a therapeutically effective amount of trimethylaminecarbmethoxyborane suspended and homogenized in a one percent solution of carboxymethyl cellulose - water carrier.

* * * * *